United States Patent [19]

Hwang et al.

[11] Patent Number: 5,851,303
[45] Date of Patent: Dec. 22, 1998

[54] METHOD FOR REMOVING METAL SURFACE CONTAMINANTS FROM SILICON

[75] Inventors: Lydia Lee-York Hwang, Midland; Arthur Francis Porsche, Midland, both of Mich.

[73] Assignee: Hemlock Semiconductor Corporation, Hemlock, Mich.

[21] Appl. No.: 642,137

[22] Filed: May 2, 1996

[51] Int. Cl.$^6$ ........................................... B08B 7/04
[52] U.S. Cl. ..................... 134/3; 134/2; 134/26; 134/28; 134/30; 436/177
[58] Field of Search ............... 134/2, 3, 26, 28, 134/30; 216/59, 73, 74, 79; 438/704; 436/177

[56] References Cited

U.S. PATENT DOCUMENTS

| | | | |
|---|---|---|---|
| 4,264,374 | 4/1981 | Beyer et al. | 134/3 |
| 4,990,459 | 2/1991 | Maeda et al. | 436/178 |

FOREIGN PATENT DOCUMENTS 54811   1/1993   Japan .

OTHER PUBLICATIONS

"Atomic Absorption Spectrochemical Analysis", B.V. L'Vov, (Adam Hilger, London) pp. 122–125 1970.
"The Wafer–surface Impurity Analysis Paradox", by Bruce E. Deal, Semiconductor International, Oct. 1990, pp. 56–57. (see Burggraaf reference submitted by applicant)

Park et al., J. Electrocehm. Soc., vol. 142 (No. 2), pp. 571–576.

Iscoff (Editor), Semiconductor International, Jul. 1993, pp. 58–63.

Burggraaf (Editor), Semiconductor International, Oct. 1990, pp. 52–58.

*Primary Examiner*—Marion E. McCamish
*Assistant Examiner*—Cheryl Juska
*Attorney, Agent, or Firm*—Richard I. Gearhart

[57] ABSTRACT

A method for removing metal surface contaminants from silicon metalloid. The method comprises sequentially contacting the silicon with gaseous hydrogen fluoride and then with an aqueous solution comprising at least one-half weight percent hydrogen peroxide. The method is especially useful as a means for recovering metal surface contaminants on semiconductor grade silicon for analysis of surface contamination of the silicon by such metals. The method is useful for recovering copper from the surface of semiconductor grade silicon in an aqueous solution which can be analyzed directly to determine the amount of copper contamination of the surface of the silicon.

20 Claims, No Drawings

METHOD FOR REMOVING METAL SURFACE CONTAMINANTS FROM SILICON

BACKGROUND OF INVENTION

The present invention is a method for removing metal surface contaminants from silicon metalloid. The method comprises sequentially contacting the silicon with gaseous hydrogen fluoride and then with an aqueous solution comprising at least one-half weight percent hydrogen peroxide. The method is especially useful as a means for recovering metal surface contaminants on semiconductor grade silicon for analysis of surface contamination of the silicon by such metals. The method is useful for recovering copper from the surface of semiconductor grade silicon in an aqueous solution which can be analyzed directly to determine the amount of copper contamination on the surface of the silicon.

The production of high density integrated circuits requires wafers of monocrystalline silicon of high purity. Metal contaminants of the silicon including, among others, copper, gold, iron, cobalt, nickel, chromium, tantalum, zinc, tungsten, titanium, magnesium, molybdenum, and aluminum can be harmful to the production of such integrated circuits. These impurities, even in small amounts, may introduce defect sites in the semiconductor grade material which can ultimately result in degraded device performance and limited circuit density. Therefore to control the quality of silicon intended for use in the semiconductor industry, methods for cleaning silicon as well as accurate methods for determining metals contamination of the surface are desired.

Methods for surface cleaning of silicon used in semiconductor devices are well known in the art. Such methods are described in Iscoff (Editor), Semiconductor International, July, 1993, pages 58–63, and include a method typically referred to as the "RCA" method. The RCA method comprises cleaning the silicon with an aqueous $H_2O_2$—$NH_4OH$ and an aqueous $H_2O_2$—HCL mixture at 75° C. to 80° C. for 10 minutes. Burggraaf (Editor), Semiconductor International, October, 1990, pages 52 to 58, further discusses such cleaning techniques. Burggraff states that although a HF-vapor process can remove native oxide layers, these processes cannot effectively remove metallic contaminates because most metals do not generate volatile species with appreciable vapor pressure. Burggraff further states that an integral deionized water rinse following exposure to vapor-phase HF cleaning can remove soluble metallic species.

Park et al., J. Electrochem. Soc., Vol. 142(No.2), pages 571 to 576, describe the use of aqueous solutions comprising HF—$H_2O$, $HNO_3$—HF—$H_2O$, or $HNO_3$—HF—$H_2O_2$ for cleaning silicon. Park et al. also describe the use of aqueous HF—$H_2O_2$ systems for cleaning silicon.

Niwayama et al., JP (Heisei) 5-4811, describe the treatment of silicon with an aqueous solution of hydrogen fluoride and hydrogen peroxide. The solution comprises by volume one portion of a 50 weight percent aqueous solution of hydrogen fluoride, 0.03 to 4 portions of a 31 weight percent hydrogen peroxide solution, and one to ten portions of water.

In a preferred embodiment of the present invention metal surface contaminants are recovered from semiconductor grade silicon in an aqueous solution, which is then analyzed by standard analytical techniques to quantify the amount of metal surface contamination of the semiconductor grade silicon. The present method offers an advantage over wet methods currently used in the art for cleaning silicon metalloid by not requiring large volumes of aqueous hydrogen fluoride. Another advantage of the present method is the ability to remove metal oxides and metals bonded directly to silicon, such as copper, from the surface of the silicon. The present method allows for essentially quantitative recovery of metal surface contaminants, such as copper, in aqueous solution from the surface of semiconductor grade silicon, and thereby provides a convenient solution for analysis of the concentrations of the removed metals.

SUMMARY OF INVENTION

The present invention is a method for removing metal surface contaminants from silicon metalloid. The method comprises sequentially contacting the silicon with gaseous hydrogen fluoride and then with an aqueous solution comprising at least one-half weight percent hydrogen peroxide. The method is especially useful as a means for recovering metal surface contaminants on semiconductor grade silicon for analysis of surface contamination of the silicon by such metals. The method is useful for recovering copper from the surface of semiconductor grade silicon in an aqueous solution which can be analyzed directly to determine the amount of copper contamination of the surface of the silicon.

DESCRIPTION OF INVENTION

The present invention is a method for removing metal contaminants from the surface of silicon metalloid. The method comprises (A) in a first step contacting silicon metalloid having a metal surface contaminant with vapor phase hydrogen fluoride and (B) in a second step contacting the silicon metalloid having the metal surface contaminant with an aqueous solution comprising at least one-half weight percent hydrogen peroxide.

The silicon metalloid (herein referred to as "silicon") from which metal surface contaminants can be remove by the present method is not limiting and can generally be any composition comprising at least 95 percent by weight of elemental silicon. A preferred silicon for use in the present invention is semiconductor grade silicon. By "semiconductor grade" silicon, it is meant a material comprising at least 99 percent by weight silicon. The physical shape of the silicon is not critical to the present invention and can be in the form of rods, wafers, chunks, and particles. The present method is especially useful for removing metal surface contaminants from silicon chunks intended for use in a process such as the Czochralski method for forming monocrystalline silicon from a melt.

In the first step of the present process, the silicon having a metal surface contaminant is contacted with hydrogen fluoride in the vapor phase. The method of contacting the silicon with the hydrogen fluoride is not critical to the present invention. It is preferred that the contact be effected in a closed vessel formed from a non-contaminating material such as Teflon® (E.I. du Pont de Nemours and Co., Wilmington, Del.). The hydrogen fluoride can be provided to the vessel either initially in the gaseous phase or as a saturated aqueous solution from which the gaseous hydrogen fluoride is evolved. Preferred is when the hydrogen fluoride is provided to the vessel as an aqueous solution from which the gaseous hydrogen fluoride then evolves. An advantage of the present invention is that it does not require large quantities of aqueous hydrogen fluoride to be effective. It is not necessary to provide the aqueous hydrogen fluoride to the vessel in a quantity sufficient to wet the surface of the silicon or to effect a rinse of the silicon. It is preferred to use volumes of aqueous hydrogen fluoride which are insufficient to wet the surface of the silicon in the vessel. Typically about 0.5 ml to 5 ml of a 50 weight percent aqueous hydrogen fluoride solution, or the equivalent thereof, per each 250 ml of container volume is considered useful in the present method. The weight and surface area of the silicon sample is not particularly critical and can be varied within wide limits. An example of a useful weight of silicon and a physical form is provided in the examples herein.

The silicon can be contacted with the hydrogen fluoride vapor at a temperature within a range of about 15° C. to 100° C. Preferred is when the silicon is contacted with the hydrogen fluoride vapor at a temperature within a range of about 20° C. to 30° C. The required length of time of contact of the silicon with the hydrogen fluoride vapor will depend to a great extent on the temperature at which the contact is effected. Generally the contact time should be at least ten minutes. Preferred is when the contact time is at least one hour and the contact temperature is within a range of about 20° C. to 30° C.

In a second step of the present method the silicon having the metal surface contaminant is contacted with an aqueous solution comprising at least one-half weight percent hydrogen peroxide. The weight percent hydrogen peroxide as used herein means the weight percent of hydrogen peroxide in the final weight of water with which the silicon is contacted. Therefore, if an aqueous solution of hydrogen fluoride is used in the first step the volume of water added during this first step would be considered as part of the total water present in the method. It is not necessary that the residual aqueous solution of hydrogen fluoride be present during conduct of the second step. However, a portion of the metal surface contaminants present on the silicon may be removed during this step and should be accounted for in any subsequent analysis.

In the present method it is preferred that the aqueous solution comprise about one to 10 weight percent hydrogen peroxide. Even more preferred is when the aqueous solution comprises about 1.5 to five weight percent hydrogen peroxide. Higher concentrations of hydrogen peroxide may be used if desired.

A sufficient volume of the aqueous solution comprising at least one-half weight percent hydrogen peroxide should be added in the second step to ensure a complete wetting of the surface of the silicon. Generally, it is preferred that at least 5 ml of the aqueous hydrogen peroxide solution be present in the method per each 100 g of silicon. Even more preferred is when at least 10 ml of the aqueous hydrogen peroxide solution is present in the method per each 100 g of silicon. The upper limit for the amount of aqueous hydrogen peroxide solution that may be added to the present method is defined by the practicality of handling the volume of the resulting aqueous phase, and by dilution considerations if the aqueous phase is to be analyzed for metals. In a preferred method, about 10 ml to 20 ml of aqueous hydrogen peroxide solution is used per each 100 g of silicon.

The temperature at which the silicon is contacted with the aqueous hydrogen peroxide solution is not critical and can generally be within a range of about 15° C. up to the decomposition temperature of the hydrogen peroxide. Preferred is when the silicon is contacted with the aqueous solution of hydrogen peroxide at a temperature within a range of about 20° C. to 30° C. The length of time the silicon is contacted with the aqueous solution of hydrogen peroxide is not critical and can generally be that required to ensure a thorough contact with the surface of the silicon. Generally a contact time of at least one minute is preferred. Even more preferred is when the silicon is contacted with the aqueous solution of hydrogen peroxide for about one to ten minutes.

The present method is especially useful for removing metal surface contaminants from silicon for determining the amount of such metals on the surface of the silicon. By the term "metal surface contaminants" it is meant any metal or metal compound present on the surface of the silicon. The present method is useful for removing all metals typically found on the surface of semiconductor grade silicon, including transition metals and heavy metals. Metals which may be removed from the silicon include copper, gold, iron, cobalt, nickel, chromium, tantalum, zinc, tungsten, titanium, magnesium, molybdenum, and aluminum. The present method is particularly effective in removing those metals from the surface of silicon where the metal is directly bonded to silicon atoms. Copper is an example of a metal which may be bonded directly to silicon atoms and which can be removed from the surface of silicon by the present method.

In a preferred embodiment of the present invention the aqueous phase containing the metal surface contaminant is analyzed to determine metal concentration. Those skilled in the art will recognize that the silicon may contain more than one metal surface contaminant and consequently the aqueous phase may contain more than one metal contaminant. The method of analyzing the aqueous phase for metal contaminants can be any of those known in the art for such analysis. If desired, the aqueous phase may be dried by evaporation to concentrate or recover the metals as a solid residue for analysis. The aqueous phase may be analyzed for metal content by such methods as graphite furnace atomic adsorption, inductive coupled plasma mass spectrometry, and ion chromatography. In a preferred method, the aqueous phase is analyzed by graphite furnace atomic absorption.

The following examples are provided to illustrate the present invention. These examples are not intended to limit the scope of the claims herein.

EXAMPLES

The ability to recover metal contaminants from the surface of semiconductor grade silicon in aqueous solutions consisting essentially of various concentrations of hydrogen peroxide was evaluated. The semiconductor grade silicon was obtained from a standard commercial process for preparing such silicon by chemical vapor deposition. The silicon was broken into pieces of a size such that three to four pieces weighed about 100 grams. Samples of approximately 100 grams of the silicon were place in 250 ml acid cleaned Teflon® containers for testing. Each silicon sample was acid cleaned by standard wet methods to remove surface contamination. Ten microliters of a standard solution containing 12 ppbw Al (ppbw=parts per billion weight), 6 ppbw Fe, 9 ppbw Zn, 6 ppbw Cu, and 9 ppbw Na were added to each sample.

About 1.5 ml of a 50 weight percent aqueous hydrogen fluoride solution was added to each silicon sample and the Teflon® container was sealed and allowed to set about 18 hours. At the end of the 18 hours, 8.3 ml of a deionized water solution consisting essentially of hydrogen peroxide at a concentration sufficient to provide a final concentration as described in Table 1 was added to the appropriate silicon samples. The hydrogen peroxide was a commercially obtained unstabilized aqueous hydrogen peroxide solution comprising about 31 to 35 weight percent of hydrogen peroxide, diluted in deionized water as required. The final concentration of hydrogen peroxide is based on the total amount of liquid added to the Teflon® container. Approximately 0.2 ml of concentrated nitric acid was added to the aqueous solution associated with each silicon sample to reduce the potential for evaporation of removed metals during analysis of the solution by graphite furnace atomic adsorption. Each Teflon® container was shaken sufficiently to insure an adequate rinse of the silicon sample.

The resulting aqueous solutions were analyzed for the metals described in Table 1 by graphite furnace atomic absorption. In Table 1 the amount of each metal recovered is reported as a percent of that added by the stock solution, corrected for background as determined by appropriate blanks.

TABLE 1

Effect of $H_2O_2$ on Metals Recovery

| $H_2O_2$ Conc. | Wt. % Metal Recovery | | | | |
|---|---|---|---|---|---|
| | Al | Fe | Zn | Cu | Na |
| 0 | 71 | 95 | 93 | 5 | 97 |
| 0 | 73 | 93 | 110 | 3 | 102 |
| 0.26 | 100 | 113 | 112 | 53 | 101 |
| 0.26 | 108 | 161 | — | 65 | 205 |
| 0.87 | 118 | 133 | 94 | 68 | 99 |
| 0.87 | 89 | 115 | 99 | 93 | 98 |
| 1.45 | 125 | 123 | 104 | 105 | 100 |
| 1.45 | 91 | 120 | 102 | 98 | 88 |
| 2.9 | 84 | 107 | 103 | 103 | 93 |
| 2.9 | 103 | 103 | 104 | 128 | 93 |

We claim:

1. A method for removing metal surface contaminants from a silicon metalloid, the method comprising:
   (A) in a first step contacting silicon metalloid having a metal surface contaminant with vapor phase hydrogen fluoride and
   (B) in a second step contacting the silicon metalloid having the metal surface contaminant with an aqueous solution consisting essentially of at least one-half weight percent hydrogen peroxide.

2. A method according to claim 1, where the silicon metalloid is semiconductor grade.

3. A method according to claim 2, where the vapor phase hydrogen fluoride is evolved from a saturated aqueous solution of hydrogen fluoride.

4. A method according to claim 3, where the silicon metalloid is contacted with vapor phase hydrogen fluoride by enclosing the silicon metalloid in a vessel containing a volume of the saturated aqueous hydrogen fluoride solution of about 0.5 ml to 5 ml per each 250 ml vessel volume.

5. A method according to claim 4, where the contact in the first step is effected at a temperature within a range of about 20° C. to 30° C.

6. A method according to claim 1, where the contact in the first step is effected at a temperature within a range of about 15° C. to 100° C.

7. A method according to claim 1, where the aqueous solution of the second step comprises about one to 10 weight percent hydrogen peroxide.

8. A method according to claim 1, where the aqueous solution of the second step comprises about 1.5 to five weight percent hydrogen peroxide.

9. A method according to claim 1, where the contacting of the second step is effected at a temperature within a range of about 15° C. up to the decomposition temperature of the hydrogen peroxide.

10. A method according to claim 1, where the volume of the aqueous solution of the second step is about 10 ml to 20 ml per each 100 g of silicon metalloid.

11. A method according to claim 1, where the metal surface contaminant is copper.

12. A method for analyzing semiconductor grade silicon for metal surface contaminants, the method comprising:
   (A) in a first step contacting semiconductor grade silicon metalloid having a metal surface contaminant with vapor phase hydrogen fluoride,
   (B) in a second step contacting the semiconductor grade silicon metalloid with an aqueous solution consisting essentially of at least one-half weight percent hydrogen peroxide thereby forming an aqueous phase containing the metal surface contaminant, and
   (C) analyzing the aqueous phase to determine metal concentration.

13. A method according to claim 12, where the silicon metalloid is contacted with vapor phase hydrogen fluoride by enclosing the silicon metalloid in a vessel containing about 0.5 to 5 ml of a saturated aqueous solution of hydrogen fluoride per each 250 ml of vessel volume and the contacting of the first step is effected at a temperature within a range of about 15° C. to 100° C.

14. A method according to claim 12, where the aqueous solution of the second step comprises about one to 10 weight percent hydrogen peroxide.

15. A method according to claim 12, where the aqueous solution of the second step comprises about 1.5 to five weight percent hydrogen peroxide.

16. A method according to claim 12, where the volume of the aqueous solution of the second step is about 10 ml to 20 ml per each 100 g of the silicon.

17. A method according to claim 12, where the contact of the second step is effected at a temperature within a range of about 20° C. to 30° C. for a period of time of about one to ten minutes.

18. A method according to claim 12, where the metal surface contaminant is copper.

19. A method according to claim 12, where the aqueous phase is analyzed by use of graphite furnace atomic adsorption.

20. A method for analyzing semiconductor grade silicon for surface contamination by copper, the method comprising:
   (A) in a first step contacting semiconductor grade silicon metalloid having copper as a surface contaminant with vapor phase hydrogen fluoride,
   (B) in a second step contacting the semiconductor grade silicon metalloid with about 10 ml to 20 ml per 100 g of silicon of an aqueous solution consisting essentially of about 1.5 to five weight percent hydrogen peroxide thereby forming an aqueous phase containing the copper, and
   (C) analyzing the aqueous phase to determine copper concentration by graphite furnace atomic absorption.

* * * * *